United States Patent [19]

Mares et al.

[11] Patent Number: 4,628,085

[45] Date of Patent: Dec. 9, 1986

[54] USE OF SILICA CATALYST FOR SELECTIVE PRODUCTION OF LACTAMS

[75] Inventors: Frank Mares, Whippany; Reginald T-H. Tang, Warren; James E. Galle, Madison; Rose M. Federici, Princeton, all of N.J.

[73] Assignee: Allied Corporation, Morris Township, Morris County, N.J.

[21] Appl. No.: 771,854

[22] Filed: Sep. 3, 1985

[51] Int. Cl.$^4$ .................. C07D 201/08; C07D 223/10
[52] U.S. Cl. ..................................... 540/539; 540/200; 540/451; 540/482; 540/488; 540/492; 546/141; 546/243; 548/553; 548/472; 548/486
[58] Field of Search ................. 260/239.3 A, 239.3 B, 260/239.3 R, 239 A; 546/243, 141; 548/553, 472, 486

[56] References Cited

U.S. PATENT DOCUMENTS 2,357,484 5/1944 Martin ........................ 260/239.3 A Primary Examiner—Robert T. Bond
Attorney, Agent, or Firm—Richard C. Stewart; Gerhard H. Fuchs

[57] ABSTRACT

A process for selective preparation of lactams which comprises contacting, in the vapor phase, an aliphatic or aromatic aminonitrile having the formula $HR_1N—D—CN$ wherein D is a divalent organic moiety and wherein $R_1$ is ($C_1$-$C_4$) alkyl or hydrogen with an effective amount of a silica catalyst, in the form of substantially spherical beads having a BET surface area greater than about 250 m$^2$/g, preferably between 300 and 500 m$^2$/g, and an average pore diameter less than about 20 nanometers preferably 8-10 nanometers at a temperature in the range of about 200° to about 400° C. and at a hydrogen or inert gas flow with a pressure in the range of about 0 to about 300 kPa, in the presence of: (a) ammonia in an amount equal to from 0 to about 50 mole percent of the molar amount of aliphatic or aromatic aminonitrile present; and (b) water in an amount from at least about 1.0 to about 50 times the molar amount of aliphatic or aromatic aminonitrile present for a time sufficient to produce the corresponding lactam is disclosed. The preferred aminonitrile is $\epsilon$-aminocapronitrile. A process for the selective conversion of aliphatic or aromatic aminonitriles having the formula $HR_1N—D—CN$ into the corresponding lactam in the presence of alkyl or aryl mononitrile or alkylene or arylene dinitriles by use of a silica catalyst, preferably a spherical silica catalyst with recovery of substantially all the alkyl or aryl mononitrile or alkylene or arylene dinitrile originally present is also disclosed.

27 Claims, No Drawings

USE OF SILICA CATALYST FOR SELECTIVE PRODUCTION OF LACTAMS

BACKGROUND OF THE INVENTION

This invention relates to the selective conversion of aliphatic and aromatic aminonitriles such as ε-aminocapronitrile into the corresponding lactams such as ε-caprolactam by employing a silica catalyst particularly a silica catalyst in the form of spherical beads having high BET surface area, narrow pore and grain size distributions.

N-substituted amides, especially 5, 6 and 7 membered lactams, are important raw materials for nylon 4, 5 and 6.

U.S. Pat. No. 2,357,484 (E. L. Martin) discloses a vapor phase process for preparing compounds containing the N-substituted amide group, for example, ε-caprolactam, by passing a vaporized mixture of water and an aliphatic amino-hydrogen-containing aminonitrile, or a vaporized mixture of water and a nitrile and amino-hydrogen-containing amine over a dehydration catalyst such as activated alumina, silica gel titanium oxide or borophosphoric acid. U.S. Pat. No. 2,357,484 also discloses that diamides are produced by passing a vaporized mixture of water and dinitriles and monoamines over the dehydration catalyst.

SUMMARY OF THE INVENTION

In accordance with one embodiment of the present invention, there is provided a process for selective preparation of lactams which comprises contacting, in the vapor phase, an aliphatic or aromatic aminonitrile having the formula $HR_1N-D-CN$, wherein D is a divalent organic moiety and wherein $R_1$ is $(C_1-C_4)$alkyl or hydrogen, with an effective amount of a silica catalyst, in the form of substantially spherical beads having a BET surface area greater than about 250 m$^2$/g and an average pore diameter less than about 20 nanometers, at a temperature in the range of about 200° to about 400° C. and at a hydrogen or an inert gas pressure in the range of about 0 to about 300 kPa, in the presence of:

(a) ammonia in an amount equal to from 0 to about 50 mole percent of the molar amount of aliphatic or aromatic aminonitrile present; and (b) water in an amount from at least about 1.0 to about 50 times the molar amount of aliphatic or aromatic aminonitrile present for a time sufficient to produce the corresponding lactam.

In accordance with another embodiment of the present invention, there is provided a process for the selective preparation of lactams which comprises contacting, in the vapor phase an aliphatic or aromatic aminonitrile having the formula $HR_1N-D-CN$, wherein D is a divalent organic moiety and wherein $R_1$ is $(C_1-C_4)$-alkyl or hydrogen, in the presence of an alkyl or aryl mononitrile or an alkylene or arylene dinitrile, with an effective amount of a silica catalyst at a temperature in the range of about 200° C. to about 400° C. and at a hydrogen or an inert gas pressure in the range of about 0 to about 300 kPa in the presence of:

(a) ammonia in an amount equal to about 0 to about 50 mole percent of the aminonitrile present; and (b) water in an amount from at least about 1.0 to about 50 times the molar amount of the aminonitrile present for a time sufficient to produce the corresponding lactam and to recover substantially all the alkyl or aryl mononitrile or the alkylene or arylene dinitrile originally present.

In accordance with still another embodiment of the present invention, there is provided a process for the selective conversion of ε-aminocapronitrile into ε-caprolactam which comprises contacting, in the vapor phase, ε-aminocapronitrile, in the presence of adiponitrile, with an effective amount of a silica catalyst at a temperature in the range of about 200° to about 400° C. and at a hydrogen or inert gas pressure in the range of about 0 to about 500 kPa in the presence of:

(a) ammonia in an amount equal to about 0 to about 50 mole percent of the ε-aminocapronitrile present; and (b) water in an amount from at least about 1.0 to about 50 times the molar amount of ε-aminocapronitrile present for a time sufficient to produce ε-caprolactam and to recover substantially all the adiponitrile initially present.

DETAILED DESCRIPTION OF THE INVENTION AND OF THE PREFERRED EMBODIMENTS

The present invention is directed to the preparation of lactams in high yield and high selectivity. We have discovered that aliphatic or aromatic aminonitriles such as ε-aminocapronitrile, are converted into the corresponding lactams with selectivities in excess of 90% by use of an effective amount of a porous silica catalyst (e.g., granular silica or especially silica in the form of substantially spherical beads,) having a BET surface area greater than about 100 m$^2$/g and a narrow pore size and grain size distributions, at a temperature ranging from about 200° to 400° C. in the presence of water vapor and optionally ammonia and/or hydrogen. It is a special feature of one embodiment of the present invention that by use of a silica catalyst in the form of substantially spherical beads having a BET surface area greater than 250 m$^2$/g and narrow pore size and grain size distributions, high percentage conversions, in excess of about 90% of aliphatic or aromatic aminonitriles into the corresponding lactams are maintained, with high selectivity, for extended reaction times without the need for reactivation of the spherical silica catalyst as was experienced with a granular, i.e., nonspherical silica catalyst having similar BET surface area, pore size and grain size, e.g., Davison Silica gel, grade 59 used in Example 2. While the prior art (U.S. Pat. No. 2,357,484) broadly discloses use of alumina, silica gel and borophosphoric acid as catalysts, only for activated alumina are experimental details provided. We have surprisingly found that porous, substantially spherical silica beads are a highly selective catalyst for production of N-substituted lactams and lactams such as epsilon-caprolactam over longer service lifetimes than observed for a granular silica catalyst having otherwise similar physical and chemical properties. While the prior art (U.S. Pat. No. 2,357,484) discloses that catalyst such as silica converts vaporized mixtures of water, amines and dinitriles into the corresponding diamides (cross condensation products), we have surprisingly found that porous silica is a highly selective catalyst for the conversion of aliphatic or aromatic aminonitriles into the corresponding lactams in the presence of alkyl or aryl mononitriles or alkylene or arylene dinitriles which are recovered substantially unchanged, (i.e., no cross condensation products were formed). In a preferred embodiment of the present invention porous silica, in the form of spherical beads having a BET surface area greater than 250 m²/g and narrow pore size and grain size distributions, was a highly selective, long-lived catalyst for conversion of ε-aminocapronitrile into ε-caprolactam even in the presence of adiponitrile, (NC—(CH₂)₄—CN), which was readily separated from the ε-caprolactam product and was recovered substantially unchanged; no cross-condensation products of ε-aminocapronitrile and adiponitrile were detected. Thus, it is believed that silica catalysts, especially the spherical silica catalyst as used in accordance with the present invention would not efficiently convert admixtures of alkyl amines and alkyl nitriles into the corresponding N-substituted amides. See Example 3.

Among the silica catalysts useful in the present invention are various acidic, neutral and basic silica catalysts such as granular silica gels which are commercially available from Alfa Ventron, e.g., #89346, The Davison Chemical Division of W. R. Grace, e.g., grades 57, and 59, as well as porous silicas having a substantially spherical shape, as described in more detail below as well as silica obtained by hydrolysis of tetralkylsilicate. However other silicas conveniently having BET surface areas of at least about 100 m²/g and pore volumes of about 1 cm³/g may also be used in the process of the present invention. Mixtures of silica with other refractory metal oxides e.g., alumina, titania, magnesia as well as these other refractory metal oxides themselves were found to deleteriously affect the process of the present invention especially when alkyl or aryl mononitriles or alkylene or arylene dinitriles were present in combination in the aliphatic or aromatic aminonitriles found useful in the present invention and the use of such mixtures are to be avoided. In a series of preliminary screening runs, selected catalysts such as acid- or base-washed titania, gamma-alumina and silica-alumina were contacted with a vaporized mixture of water and adiponitrile (ADN) in the presence of ammonia and hydrogen at 250° C. to 300° C. In these runs, conducted with these selected catalysts (disclosed in U.S. Pat. No. 2,357,489), it was found that 45–95% of the ADN was degraded to cyclopentanone.

The silica catalysts found especially useful in the process of the present invention are free flowing powders having a substantially spherical shape by transmission electron microscopy, a BET surface area greater than 250 m²/g, preferably greater than about 300 m²/g and more preferably about 300–500 m²/g, a narrow average pore size or pore diameter of less than about 20 nanometers, preferably in the range of 8-15 nanometers. The spherical silica catalyst manufactured by Pechiney - Saint Gobain, France, under the tradename Spherosil and distributed in the United States by Waters Associates, Inc., Milford, Mass. 01757 under the registered trademark PORASIL® may be conveniently used. Particularly suitable silica catalysts are Spherosil, grade XOA400 and PORASIL A. The spherical silica grains or beads useful in the present invention may be conveniently prepared by calcination at 400°–800° C. of silica gel in the form of small spheres obtained by precipitation of alkali metal silicates or alkyl orthosilicates with mineral acids, e.g., H₂SO₄ in a liquid immiscible with water (or by crushing the gel in mass) followed by washing, under controlled pH conditions, so that 0.1–5 wt % of alkali metal oxide, e.g., Na₂O, remains. See Chemical Abstracts, Vol. 67, 66123G (1967) and British Pat. No. 1,171,651, published 11/26/69 (issued to M Le Page et al. of Pechiney Saint - Gobain). The preparation of spherical silica, e.g., PORASIL A, from sulfuric acid and sodium silicate is also disclosed by C. J. Walling in J. Amer. Chem. Soc., Vol. 72 (1952), 4464.

The process of the present invention for the highly selective production of lactams is conveniently operated by placing the silica catalyst in the form of a powder (e.g., 80–100 mesh) in a flow reactor which normally contains quartz chips used for vaporization and dispersion of the reactants.

Temperatures in the range of about 200° to 400° C., preferably about 250° to about 350° C. are adequate for the preparation of N-substituted amides. Contact times are not critical. Contact times of about 1 to about 10 seconds are preferred.

The reaction for the preparation of lactams may be conducted in a flow reactor in the presence of a hydrogen or inert gas such as nitrogen having a pressure in the range of about 0 to about 300 kPa, preferably 50 to about 150 kPa. Ammonia may be present in an amount equal to about 0 to about 50 mol percent of the aliphatic or aromatic aminonitrile such as ε-aminocapronitrile present. Water may be present in the reaction mixture in an amount from at least about 1.0 to about 50 times the molar amount of the aminonitrile.

Water in combination with an aliphatic or aromatic aminonitrile is introduced in the form of the vapor into the reaction zone optionally in the presence of gaseous ammonia and hydrogen.

In the embodiments of the present invention wherein dinitrile is present, the ratio of aminonitrile to dinitrile may be varied from about 99:1 to about 1:99 (v/v), and preferably is about 50:50 to 90:10.

The aliphatic or aromatic aminonitriles useful in the process of the present invention have the formula HR₁N—D—CN wherein D is a divalent organic moiety having the formula:

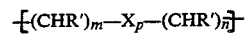

wherein X is O or NR' or ortho-phenylene, wherein R' is independently hydrogen or (C₁-C₈) alkyl or (C₁-C₈) alkenyl or (C₂-C₈) alkyloxyalkyl, wherein n and m are from 1 to 5 with the proviso that $n+m=3, 4, 5$ or 6, and wherein p is 0 or 1 and wherein R' is (C₁-C₄)alkyl or hydrogen.

The orthophenylenes have the formula:

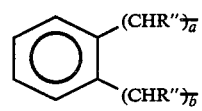

wherein R" is independently hydrogen, or (C₁-C₃) alkyl and wherein a and b are integers of 0 to 3 selected so that $a+b=1, 2$ or 3.

Among the omega-aminonitriles found especially useful in the process of the present invention are H₂N—(CH₂)₃—CN, H₂N—(CH₂)₄—CN, H₂N—(CH₂)₅CN, (CH₂)₂—O—H₂N—(CH₂)₃O—CH₂—CN, H₂N—(CH₂)₂—O—CH₂—CN, H₂N—(CH₂)₃—O—(CH₂)₃CN, H₂N—(CH₂)₂—O—(CH₂)₂—CN, H(CH₃)N—(CH₂)₃—CN, H(C₂H₅)N—(CH₂)₃—CN, H(n—C₃H₇)N—(CH₂)₃—CN, H(i—C₄H₉)N—(CH₂)₃—CN, H(CH₃)N—(CH₂)₄—CN, H(C₂H₅)N—(CH₂)₄—CN, H(i—C₃H₇)N—(CH₂)₄—CN, H(n—C₄H₉-

)N—(CH$_2$)$_4$—CN, H(CH$_3$)N—(CH$_2$)$_5$—CN, H(C$_2$H$_5$)N—(CH$_2$)$_5$—CN, H(i—C$_3$H$_7$)N—(CH$_2$)$_5$—CN, and H(n—C$_4$H$_7$)N—(CH$_2$)$_5$—CN,

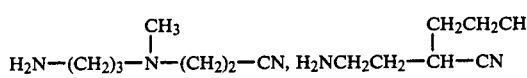

and orthophenylenes such as H$_2$N—(CH$_2$)$_2$—C$_6$H$_4$—CH$_2$—CN, H$_2$N—CH$_2$—C$_6$H$_4$—(CH$_2$)$_2$—CN or H$_2$N—CH$_2$—CH(CH$_3$)—C$_6$H$_4$—CH$_2$CN or amino alkyloxyalkylnitriles such as H$_2$N—CH(CH$_3$)CH$_2$—O—CH(C$_2$H$_5$)CN.

Other aminonitriles obvious in view of this disclosure are considered within the scope of the present invention so long as the aminonitrile and corresponding lactam have vapor pressures sufficient to remain in the gaseous state under the conditions of the present invention. The preferred aminonitriles are H$_2$N—(CH$_2$)$_n$CN wherein n is 3, 4 or 5.

The process of this invention can be carried out in the presence of alkyl and aryl mononitriles, and alkylene and arylene dinitriles without deleteriously affecting the process. Illustrative of such alkyl and aryl mononitriles are acetonitrile, butyronitrile, benzylnitrile, and the like. Suitable alkylene and arylene dinitriles include those of the formula:

NC—D'—CN

Wherein D' is as D described above, such as NC—(CH$_2$)$_2$—CN, NC—(CH$_2$)$_3$—CN, NC—(CH$_2$)$_4$—CN, NC—(CH$_2$)$_3$—O—(CH$_2$)$_3$—CN, NC—(CH$_2$)$_5$—CN, CH$_3$—C$_6$H$_4$—(CH$_2$)$_2$—CN and NC—CH$_2$C$_6$H$_4$—(CH$_2$)$_2$—CN.

GENERAL EXPERIMENTAL

Characterization of PROASIL ® A and Davison Silica Gel Grade 59

A virgin sample of PORASIL A was found to be more acidic than other commercial available silica gels and contain a number of strongly acidic Bronsted acid sites which might be associated with aluminum oxide bonded to silicon. See J. N. Armor et al., *Journal of Catalysis*, Vol. 73, pages 57–65 (1982) at pages 60–63. Virgin samples of PORASIL A and Davison Silica gel Grade 57 (similar to grade 59) were analyzed and found to contain the elements listed in Table I below, other than silicon and oxygen.

TABLE I

| | PORASIL A | Davison Grade 57 | Davison Grade 59[e] |
|---|---|---|---|
| BET SA[a] (m$^2$/g) | 440 | 300 | 340 |
| AVG P.D.[b] (nm) | 10 | 1 | 14 |
| PV[c] (cc/g) | 1.0 | 1.0 | 1.15 |
| Element (wgt %) | | | |
| Al | 0.1 | <.01 | 0.1[f] |
| Ba | N.D.[d] | —[d] | — |
| Ca | 0.1 | 0.1 | .01[g] |
| C | 1.15 | — | — |
| Cu | <0.01 | <0.01 | — |
| Fe | 0.01–.1 | <0.01 | — |
| Mg | <.01 | .01–0.1 | — |
| Mo | — | <.01 | — |
| Na | 0.1 | — | 0.06[h] |
| S | .33 | — | — |
| Ti | .1 | <<.01 | .02[i] |
| K | 0.001 | — | — |
| H | 1.15 | — | —[j] |
| N | 0.13 | | |

TABLE I-continued

| | PORASIL A | Davison Grade 57 | Davison Grade 59[e] |
|---|---|---|---|
| Zr | — | | 0.03[k] |
| Trace Elements | | | 0.03 |

Footnotes to Table I
[a]BET Surface area measured by N$_2$ desorption using a Quantasorb and BET procedure of S. Brunaver et al. J.A.C.S., (1938), 60, 309.
[b,c]average pore volume and average pore diameter calculated from mercury porosimetry data obtained with a Quantachrome Mercury Porosimeter
[d]ND = not detectable, i.e., <.01%; — means not determined
[e]Reproduced from "Technical Bulletin" obtained from W. R. Grace, Davison Chemical Division, Industrial Chemicals Dept., entitled "New Absorption Date from Industrial Chemicals Department 1C-11-80.
[f]as Al$_2$O$_3$
[g]as CaO
[h]as Na$_2$O
[i]as TiO$_2$
[j]measured on dry sample
[k]as ZrO$_2$

EXAMPLE 1

Conversion of epsilon-Aminocapronitrile into epsilon-Caprolactam in the presence of Porasil A This Example illustrates that relatively constant conversion of 6-aminocapronitrile into caprolactam was maintained using as catalyst, the spherical material PORASIL ® A (Waters Assoc., Inc.). The PORASIL A catalyst was obtained as a powder (80–100 mesh) and used as such. The catalyst (9 mL, 4.09 g) was placed in a flow reactor on top of a glass fritted disc. Quartz chips (2 g), used for vaporization and dispersion of the reactants during the run, were placed on top of the catalyst. The reactor was heated rapidly to 300° C. with an initial gas flow at a low (e.g., 10% H$_2$, 90% N$_2$) H$_2$/N$_2$ ratio. The hydrogen content in the gas was raised to 100% H$_2$ in those cases where H$_2$ was used as a component in the reaction; otherwise 100% nitrogen was used. A temperature of 300° C. was maintained as the reaction temperature, and the appropriate gas and reactant liquid feeds were started.

The gas flow and feed conditions were:
H$_2$—49 gas mL/min (76.9 volume %)
NH$_3$—4 gas mL/min (6.3 volume %)
6-aminocapronitrile—6.5×10$^{-3}$ liquid mL/min (1.9 volume %)
H$_2$O—7.6×10$^{-3}$ liquid mL/min (14.9 volume %).
contact time—4.2 sec.

The gas flows were regulated by appropriate Tylan flow controllers. The liquid reactants were delivered by Sage Syringe Pumps. The products were collected in round-bottom flasks (kept at Dry Ice temperatures) with gas release side arms. Product samples were diluted with methanol for g.l.c. analysis with triglyme being used as an internal standard for quantitative analysis. The results are tabulated in Tables IIa and IIb.

It is important to note that virgin catalyst used in Run #1 was employed, without reactivation in Runs #2–7. Thus, the % conversion of 87% and % selectivity to lactam of 96.5% (reported in Run #7) were achieved after a service time of about 150 hrs for the same PORASIL catalyst; no reactivation was necessary. Thus, the catalytic activity of PORASIL A (as measured by % conversion and % selectivity) remained relatively constant over extended reaction times. See Example 2 hereinbelow

Tables IIa and b

Conversion of ε-aminocapronitrile into ε-caprolactam in the presentce of PORASIL A Catalyst of Example 1 to 300° C.

TABLE IIa

| Run # | Time[a] (min) | Reaction Conditions | | | | |
|---|---|---|---|---|---|---|
| | | $H_2$ (vol %) | $N_2$ (vol %) | $NH_3$ (vol %) | $H_2O$ (vol %) | Substrate (vol %) |
| 1 | 1246 | 76.9 | 0 | 6.3 | 14.9 | 1.9 |
| 2 | 1262 | 76.9 | 0 | 6.3 | 14.9 | 1.9 |
| 3 | 1246 | 76.9 | 0 | 6.3 | 14.9 | 1.9 |
| 4 | 1262 | 76.9 | 0 | 6.3 | 14.9 | 1.9 |
| 5 | 1277 | 76.9 | 0 | 6.3 | 14.9 | 1.9 |
| 6 | 1231 | 76.9 | 0 | 6.3 | 14.9 | 1.9 |
| 7 | 1262 | 76.9 | 0 | 6.3 | 14.9 | 1.9 |

[a]Each run was made with the apparatus and catalyst used in Run #1. After each run, the organic substrate feed valve was closed and the catalyst was treated in the same apparatus for 6-10 hours under conditions of the previous run. Then, the valve for organic substrate feed was opened and the new Run was started. Thus after Run #1, the organic substrate feed was stopped and the catalyst was treated at 300° C. for 10 hours with $H_2$ and $NH_3$ and $H_2O$. The products were then collected and the yield determined. Thus, the sum of the Run times reflects only the total contact time of catalyst while the organic substrate was being added into the reactor.

TABLE IIb

| Run # | Conversion (%) | Products of Reaction | | | |
|---|---|---|---|---|---|
| | | Material Balance[f] (vol) | Lactam[b] (%) S[c,f] (vol) | Imine[d] (%) S[c] (vol) | Cpone[e] (%) S[c] (vol) |
| 1 | 92.0 | 103.0 | 101 | 2.3 | 0.3 |
| 2 | 88.5 | 93.6 | 90.1 | — | — |
| 3 | 87.9 | 94.2 | 90.5 | — | — |
| 4 | 88.3 | 95.4 | 91.9 | 0.8 | 0.3 |
| 5 | 88.5 | 98.5 | 95.1 | 0.3 | 0.2 |
| 6 | 90.4 | 94.0 | 91.4 | 1.7 | 0.2 |
| 7 | 87.0 | 99.9 | 96.5 | — | — |

[b]epsilon-caprolactam
[c]% selectivity
[d]hexamethyleneimine
[e]cyclopentanone
[f]due to experimental difficulties in measurements of the liquid reactant volumes in the syringes, errors in the Material Balances and Selectivities were estimated to be ± 4%

EXAMPLE 2

The procedure and apparatus of Example 1 were employed to convert ε-aminocapronitrile into ε-caprolactam in the presence of 9 mL (3.05 g) of Davison Silica gel, grade 59 (Buffer Grade) (80-100 mesh) obtained from W. R. Grace, Davison Chemical Div., Baltimore, Md. 21203. The results are summarized in Tables IIIa and IIIb.

Tables IIIa and b

Conversion of ε-aminocapronitrile into ε-caprolactam in the Presence of Davision Silica gel 59 at 300° C.

TABLE IIIa

| Run # | Time[a] (min) | Reaction Conditions | | | | |
|---|---|---|---|---|---|---|
| | | $H_2$ (vol %) | $N_2$ (vol %) | $NH_3$ (vol %) | $H_2O$ (vol %) | Substrate (vol %) |
| 8 | 1385 | 76.8 | 0 | 6.3 | 15.0 | 1.9 |
| 9 | 1262 | 76.8 | 0 | 6.3 | 15.0 | 1.9 |
| 10 | 1292 | 76.8 | 0 | 6.3 | 15.0 | 1.9 |
| 11 | 1277 | 76.8 | 0 | 6.3 | 15.0 | 1.9 |
| 12 | 1262 | 76.8 | 0 | 6.3 | 15.0 | 1.9 |
| 13 | 1262 | 76.8 | 0 | 6.3 | 15.0 | 1.9 |

[a]The catalyst used in run #8 was used in each successive run (#9-13). See Footnote a to Table IIa for appropriate experimental procedure.

TABLE IIIb

| Run # | Conversion (%) | Products of Reaction | | | |
|---|---|---|---|---|---|
| | | Material Balance[e] (%) | Lactam[b,e] (% S) | Imine[c] (% S) | Cpone[d] (% S) |
| 8 | 87.1 | 92.9 | 90.1 | 1.3 | 0.4 |
| 9 | 77.5 | 98.7 | 95.6 | 2.3 | 0.4 |
| 10 | 70.8 | 99.2 | 95.7 | 2.6 | 0.6 |
| 11 | 65.5 | 100 | 98.3 | 2.0 | trace |
| 12 | 63.4 | 99.1 | 95.5 | trace | trace |
| 13 | 57.4 | 97.7 | 93.0 | trace | trace |

[b]epsilon-caprolactam
[c]hexamethyleneimine
[d]cyclopentanone
[e]See Footnote f to Table IIb This Example illustrates that aliphatic aminonitrile can be converted into the corresponding lactam with high selectivities in excess of 90% by use of granular, i.e., nonspherical silica gel catalyst. However, unlike the spherical silica gel catalyst, such as Porosil A, the percent conversions of aminonitrile into the corresponding lactam decreased with time. It is believed that high percent conversion of aminonitrile into the corresponding lactam could be maintained over extended reaction times with high selectiveties in excess of 90% by reactivation or replacement of these granular silica gel catalyst.

EXAMPLE 3

Conversion of 70:30 Mixture of ε-Aminocapronitrile:Adipontrile into ε-Caprolactam in the presence of Porasil A The apparatus and procedure were the same as in Example 1 in all respects except that a 70:30 (v/v) mixture of ε-aminocapronitrile:adiponitrile was fed as the organic substrate to the reactor. The results summarized in Tables IVa and IVb and V indicate that high selectivity for aminonitrile conversion into ε-caprolactam can be obtained even in the presence of adipontrile. The adiponitrile was substantially unchanged. Accordingly, the recovery of adiponitrile from caprolactam product was simplified. Similar results are expected for mixtures of ε-aminocapronitrile:adiponitrile in the ratios of 1:99 to 99:1.

Tables IVa and b conversion of 70:30 v/v mixture of ε-aminocapronitrile:adiponitrile into ε-caprolactam in the presence of PORASIL A catalyst at 300° C.

TABLE IVa

| Run # | Time (min) | Reaction Conditions | | | | |
|---|---|---|---|---|---|---|
| | | $H_2$ (vol %) | $N_2$ (vol %) | $NH_3$ (vol %) | $H_2O$ (vol %) | Substrate (vol %)[c] |
| 14 | 1260[a] | 75.8 | 0 | 6.7 | 16.1 | 1.4 |
| 15 | 962 | 75.8 | 0 | 6.7 | 16.1 | 1.4 |
| 16 | 1511 | 75.8 | 0 | 6.7 | 16.1 | 1.4 |
| 17 | 1356 | 0 | 75.8 | 6.7 | 16.1 | 1.4 |
| 18 | 1418 | 75.8[b] | 0 | 6.7 | 16.1 | 1.4 |
| 19 | 1800 | 64.5[b] | 0 | 5.7 | 27.4 | 2.4 |

[a]catalyst used in Run #14 was used for Runs #15-19 without reactivation. See footnote a to Table IIa for appropriate experimental procedure.
[b]Runs #18 and 19 were done at 350° C.
[c]ε-aminocapronitrile:adiponitirle (70:30 v/v)

TABLE IVb

Reaction Products[a]

| Run # | Conversion[f] (%) | Material Balance[f] (%) | Lactam[b,f] % S | Imine[c] % S | Cpone[d] % S | % Unconverted ADN[e,f] |
|---|---|---|---|---|---|---|
| 14 | 63.1 | 103 | 102 | 0.3 | 1.3 | 112 |
| 15 | 62.1 | 107[g] | 107 | 0.0 | 1.2 | 108.1 |
| 16 | 61.3 | 102 | 96.2 | 0.4 | 2.1 | 102.8 |
| 17 | 60.7 | 104 | 96.9 | 0.0 | 2.0 | 102.2 |
| 18 | 52.9 | 104 | 100 | 0.7 | 2. | 105.7 |
| 19 | 50.8 | 99.4 | 84.3 | 0.8 | 5.4 | 96.6 |

[a] % Conversion and % material balance are based on total organic feed; % S to Lactam, Imine and Cpone are based on aminocapronitrile consumed.
[b] ε-caprolactam
[c] hexamethyleneimine
[d] cyclopentanone
[e] adiponitrile (ADN)
[f] See Footnote f to Table IIb.
[g] larger error due to plugging of syringe used to deliver liquid reactants.

TABLE V

Comparison of Amount of Adiponitrile in Feed and Product of Example 3

| Run # | ADN[a] in Feed (mmol) | ADN[a] in Product (mmol) |
|---|---|---|
| 14 | 14.96 | 16.74 |
| 15 | 11.42 | 12.34 |
| 16 | 17.94 | 18.44 |
| 17 | 16.09 | 16.45 |
| 18 | 16.83 | 17.80 |
| 19 | 21.35 | 20.62 |
| TOTAL | 98.59[b] | 102.35[b] |

[a] adiponitrile (ADN)
[b] See footnote f to Table IIb.

The adiponitrile was recovered from the ε-caprolactam product, in an amount substantially equivalent to that initially present in the feed. Thus, the adiponitrile is not consumed under conditions that converted ε-aminocapronitrile selectively into ε-caprolactam. No cross-condensation products were detected.

We claim:

1. A process for selective preparation of lactams which comprises contacting, in the vapor phase, an aliphatic or aromatic aminonitrile having the formula $HR_1N-D-CN$, wherein D is a divalent organic moiety and wherein $R_1$ is $(C_1-C_4)$alkyl or hydrogen, with an effective amount of a silica catalyst, in the form of substantially spherical beads having a BET surface area greater than about 250 m$^2$/g and an average pore diameter less than about 20 nanometers at a temperature in the range of about 200° to about 400° C. and at a hydrogen or inert gas pressure in the range of about 0 to about 500 kPa, in the presence of:

(a) ammonia in an amount equal to from 0 to about 50 mole percent of the molar amount of aliphatic or aromatic aminonitrile present; and (b) water in an amount from at least about 1.0 to about 50 times the molar amount of aliphatic or aromatic aminonitrile present for a time sufficient to produce the corresponding lactam.

2. The process of claim 1 wherein hydrogen or inert gas is present in an amount sufficient to maintain the pressure at a value in the range of about 50 to about 300 kPa.

3. The process of claim 1 wherein the silica catalyst has a BET surface area greater than about 300 m$^2$/g and an average pore diameter of about 8–10 nanometers.

4. The process of claim 3 wherein the silica catalyst has a BET surface area between about 300 and 500 m$^2$/g.

5. The process of claim 1 wherein the divalent organic moiety D has the formula:

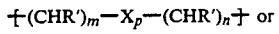 or

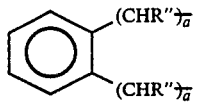

wherein:

X is o or—$NR^1$;

R' is independently hydrogen or $(C_1-C_8)$ alkyl or $(C_1-C_8)$ alkenyl or $(C_2-C_8)$ alkoxyalkyl;

R" is independently hydrogen or $(C_1-C_3)$ alkyl;

a and b are individually integers from 0 to 3, with the proviso that $a+b=1$, 2 or 3;

n and m are individually integers from 0 to 6, provided that $n+m=3$, 4, 5 or 6; and p is 0 or 1.

6. The process of claim 5 wherein D is of the formula:

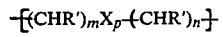

wherein:

R' is $(C_1-C_4)$ alkyl or hydrogen.

7. The process of claim 6 wherein R' is $(C_1-C_4)$alkyl.

8. The process of claim 6 wherein R' is hydrogen.

9. A process for the selective conversion of ε-aminocapronitrile into ε-caprolactam which comprises contacting, in the vapor phase, ε-aminocapronitrile, in the presence of adiponitrile, with an effective amount of a silica catalyst at a temperature in the range of about 200° to about 400° C. and at a hydrogen or inert gas pressure in the range of about 0 to about 500 kPa in the presence of:

(a) ammonia in an amount equal to about 0 to about 50 mole percent of the ε-aminocapronitrile present; and (b) water in an amount from at least about 1.0 to about 50 times the molar amount of the aminocapronitrile present for a time sufficient to produce ε-caprolactam and to recover substantially all the adiponitrile initially present.

10. The process of claim 9 wherein hydrogen or inert gas is present in an amount sufficient to maintain the pressure at a value in the range of about 50 to about 300 pka.

11. The process of claim 9 wherein ammonia is present.

12. The process of claim 9 wherein the silica catalyst is in the form of substantially spherical beads having a BET surface area greater than about 250 m$^2$/g and an average pore diameter of less than about 20 nanometers.

13. The process of claim 12 wherein the silica catalyst has a BET surface area greater than about 300 m$^2$/g and an average pore diameter of about 8–10 nanometers.

14. The process of claim 12 wherein the silica catalyst has a BET surface area between about 300 and 500 m$^2$/g.

15. A process for the selective preparation of lactams which comprises contacting, in the vapor phase an aliphatic or aromatic aminonitrile having the formula $HR_1N-D-CN$, wherein D is a divalent organic moiety and wherein R is $(C_1-C_4)$-alkyl or hydrogen, in the presence of an alkyl or aryl mononitrile or an alkylene or arylene dinitrile, with an effective amount of a silica catalyst at a temperature in the range of about 200° C. to about 400° C. and at a hydrogen or an inert gas pressure in the range of about 0 to about 500 kPa in the presence of:
  (a) ammonia in an amount equal to about 0 to about 50 mole percent of the aminonitrile present; and
  (b) water in an amount from at least about 1.0 to about 50 times the molar amount of the aminonitrile present,
for a time sufficient to produce the corresponding lactam and to recover substantially all the alkyl or aryl mononitrile or alkylene or arylene dinitrile originally present.

16. The process of claim 15 wherein hydrogen or inert gas is present in an amount sufficient to maintain the pressure at a value in the range of about 50 to about 300 kPa.

17. The process of claim 15 wherein ammonia is present.

18. The process of claim 15 wherein a granular silica catalyst is used.

19. The process of claim 15 wherein a silica catalyst in the form of substantially spherical beads having a BET surface area greater than about 250 m²/g and an average pore diameter of less than 20 nanometers is used.

20. A process according to claim 15 wherein said process is carried out in the presence of one or more alkylene or arylene dinitrile.

21. A process according to claim 19 wherein said dinitrile is of the formula:

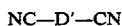

NC—D'—CN wherein D' is a divalent organic moiety of the formula:

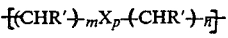 or

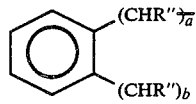

wherein:
X is O, or —NR′;
R′ is independently hydrogen, $(C_1-C_8)$ alkyl, $(C_1-C_8)$ alkenyl, or $(C_2-C_8)$ alkoxyalkyl;
n and m are the same or different and are integers from 0 to 6 with the proviso that n+m is 3, 4, 5 or 6;
p is 0 or 1;
R″ is independently hydrogen, or $(C_1-C_3)$ alkyl; and
a and b the same or different and are integers from 0 to 3 with the proviso that $a+b=1, 2$ or 3.

22. A process according to claim 21 wherein D is the same as D′.

23. A process according to claim 22 wherein D is of the formula:

$-(CHR')_m X_p (CHR')_n-$ wherein: R′ is $(C_1-C_3)$ alkyl or hydrogen.

24. A process according to claim 1 wherein said silica catalyst contains from about 0.1 to about 5 wt % of alkali metal oxide.

25. A process according to claim 24 wherein said alkali metal is sodium.

26. A process according to claim 1 wherein said silica catalyst is prepared by calcination of silica gel in the form of spheres at a temperature of from about 400° C. to about 800° C., or by crushing said gel and washing said crushed gel under control p. 4.

27. A process according to claim 26 wherein said silica gel is formed by precipitation of alkali metal silicates or alkyl ortho-silicates with a mineral acid in a liquid immiscible with water.

* * * * *